(12) United States Patent
Huber et al.

(10) Patent No.: US 11,497,625 B2
(45) Date of Patent: Nov. 15, 2022

(54) SURGICAL TOOL

(71) Applicant: Oxford University Innovation Limited, Oxford (GB)

(72) Inventors: John Huber, Oxford (GB); Dale Line, Oxford (GB); Katharine Weld, Oxford (GB); Chris Huber, Isleworth (GB); Khaled Sarraf, London (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 16/763,244

(22) PCT Filed: Nov. 13, 2018

(86) PCT No.: PCT/GB2018/053271
§ 371 (c)(1),
(2) Date: May 12, 2020

(87) PCT Pub. No.: WO2019/097214
PCT Pub. Date: May 23, 2019

(65) Prior Publication Data
US 2021/0169662 A1 Jun. 10, 2021

(30) Foreign Application Priority Data
Nov. 14, 2017 (GB) .................................... 1718768

(51) Int. Cl.
*A61F 2/46* (2006.01)
*A61F 2/36* (2006.01)
(52) U.S. Cl.
CPC .......... *A61F 2/4637* (2013.01); *A61F 2/4607* (2013.01); *A61F 2002/365* (2013.01);
(Continued)

(58) Field of Classification Search
CPC ................. A61F 2/4637; A61F 2/4607; A61F 2002/3611; A61F 2002/3625;
(Continued)

(56) References Cited

U.S. PATENT DOCUMENTS 3,981,308 A * 9/1976 Schlein .............. A61B 17/2804
606/205
4,922,770 A * 5/1990 Dlugolecki ............... B25B 7/10
81/325
(Continued)

FOREIGN PATENT DOCUMENTS

EP 1 106 148 A1 6/2001
EP 1 519 686 B1 4/2005
(Continued)

OTHER PUBLICATIONS

International Search Report & Written Opinion for WO2019/097214 (PCT/GB2018/053271), dated Mar. 15, 2019, pp. 1-9.
(Continued)

*Primary Examiner* — Jennifer Dieterle
*Assistant Examiner* — Mihret Tafesse
(74) *Attorney, Agent, or Firm* — Thomas|Horstemeyer, LLP

(57) ABSTRACT

A surgical tool for separating two components, for example removing a femoral head from a femoral stem, having a four bar chain whose four bars are a first handle (L1), an crossover component (L2), a second handle (L3) and a crossbar (L4) pivotally connected respectively by: a first joint (J1) between the first handle and the crossover component; a second, crossover joint (J2) between the crossover component and the second handle; a third joint (J3) between the second handle and the crossbar, and a fourth joint (J4) between the crossbar and the first handle, and wherein, upon application of a gripping force to the first and second handles, the first and second jaws separate from one another so as to separate the two components engaged therewith.

18 Claims, 8 Drawing Sheets

(52) U.S. Cl.
CPC .......... *A61F 2002/3611* (2013.01); *A61F 2002/3625* (2013.01); *A61F 2002/4628* (2013.01); *A61F 2002/4641* (2013.01)

(58) Field of Classification Search
CPC ........ A61F 2002/365; A61F 2002/4628; A61F 2002/4641; A61F 2002/30537; A61B 17/2804
See application file for complete search history.

(56) References Cited

U.S. PATENT DOCUMENTS

| | | | |
|---|---|---|---|
| 5,944,723 A | 8/1999 | Colleran et al. | |
| 10,492,929 B2 * | 12/2019 | Termanini | A61F 2/4607 |
| 2002/0004684 A1 | 1/2002 | Thomas et al. | |
| 2007/0005145 A1 | 1/2007 | Banks et al. | |
| 2011/0308057 A1 * | 12/2011 | Abrams | B25B 7/02 |
| | | | 29/426.5 |

FOREIGN PATENT DOCUMENTS

| | | |
|---|---|---|
| JP | H05 93412 A | 4/1993 |
| WO | 2017/019325 A1 | 2/2017 |
| WO | 2017/030925 A1 | 2/2017 |
| WO | 2018/026430 A1 | 2/2018 |

OTHER PUBLICATIONS

UK Search Report for GB1718768.3, dated Apr. 27, 2018, pp. 1-7.
International Preliminary Report on Patentability for WO2019/097214 (PCT/GB2018/053271), dated May 19, 2020, pp. 1-7.
European Office Action for Application No. 18 808 056.8, dated May 17, 2022, pp. 1-8.

* cited by examiner

SURGICAL TOOL

CROSS-REFERENCE TO RELATED APPLICATIONS

This application is the National Stage of International Application No. PCT/GB2018/053271, filed Nov. 13, 2018, which claims priority to GB 1718768.3, filed Nov. 14, 2017, which are entirely incorporated herein by reference.

This invention relates to a surgical tool for removing a femoral head from a femoral stem in total hip arthroscopy revision surgery.

BACKGROUND

Hip replacement, or arthroplasty, is a surgical procedure in which the damaged or diseased hip joint is replaced by a new prosthetic implant. The procedure is most commonly performed on people between the ages of 60 and 80, generally due to osteoarthritis or in some cases, hip fractures. The purpose of the procedure is primarily to relieve pain and improve the function and mobility of the hip.

The procedure begins with the surgeon making a 15-20 cm incision over the side of the hip through the muscles, after which they remove the diseased bone tissue and cartilage from the hip joint. The head of the femur is removed and the interior of the femur is hollowed and shaped to fit the artificial stem. The head of the femur and the acetabulum are then replaced with two prosthetic parts, with the prosthetic femoral head being joined to the prosthetic stem by a Morse taper. Friction, created by the shearing of the wall of a bore in the head as it is pushed onto a trunnion on the stem, causes an interference fit and cold-welding between the two components, which increases during physiological loading. The shear stress at the trunnion-bore interface causes friction between the taper surfaces which also provides resistance to separation.

The stem and acetabulum may be cemented into place or uncemented. Cemented parts are fastened to existing healthy bone with, for example, polymethylmethacrylate (PMMA) cement. Uncemented parts depend on a process called biologic fixation to hold them in place. This means the parts are made with a porous surface that allows the bone to grow into the pores and hold the new parts in place.

In 2013, just over one in ten of approximately 80,000 total hip arthroplasties performed in the UK were revision surgeries. Hip revision surgery is performed to replace worn out, loose, painful, or infected prostheses.

A problem occurs when the femoral head has become worn or damaged and needs replacing but the stem is still in good condition. The force required to remove the head often exceeds the force required to move the stem, resulting in unwanted displacement of the stem. In particular, torsional force on the stem is highly undesirable as that may result in displacement or accidental dislodging of the stem, or even fracture of the femur. If the stem is displaced, a new stem needs to be inserted which requires more original bone to be removed from inside the femur.

In new implants, a polymer trial head is first used to test for correct positioning. The trial head must then be removed in order to put the working prosthetic head in place. In this situation, also, it may be difficult to remove the trial head from the implanted stem.

There are various known ways that surgeons currently use to remove femoral heads. Crudely striking the head with an oblique-angled chisel or punch to remove it from the stem risks unwanted forces on the stem as outlined above. Attempting to twist and pull the head off the stem by hand risks unwanted torsional force on the stem, or the surgeon being unable to apply sufficient force manually.

Another possibility is to heat the femoral head to use thermal expansion to facilitate extraction of the head from the stem, see "Thermal expansion modular femoral head extractor for revision total hip arthroplasty". J Arthroplasty. 1995 August; 10(4):476-9, Robinson R P, Simonian P T.

Some femoral head separator tools are known. Those which apply an axial force to the femoral head, away from the stem, are relatively cumbersome and access to the head from the axial direction is difficult. These tools may not be able to be used at all on smaller patients. Tools which approach the head from a lateral direction are preferred but these generally comprise some kind of wedge arrangement wherein a screw threaded shaft pushes a wedge against the femoral head to provide an axial force away from the stem. A problem with this type of tool is that force is only applied to one side of the femoral head and damage to the stem may also occur. Furthermore, the mechanical advantage is fixed and cannot be modified by the surgeon. Also, since the wedges have to slide over the implant components, the components may be marked or otherwise damaged.

Another disadvantage of known tools is that they may be specialised for a particular design of hip implant and thus not useful for the wide range of hip implants which may be encountered in revision surgery.

There is therefore a need for an improved surgical tool for removing a femoral head prosthesis from its femoral stem.

BRIEF SUMMARY OF THE DISCLOSURE

The invention is defined in the appended claims. In a first aspect of the invention there is provided a surgical tool for separating two components, for example removing a femoral head from a femoral stem, the tool comprising:

first and second handles with a crossbar therebetween, the handles being adapted to be moveable towards one another when gripped by a user;

a crossover component;

first and second jaws adapted to engage the two components to be separated, wherein the first jaw is integral with or mounted on the crossover component and the second jaw is integral with or mounted on the second handle, wherein the tool comprises a four bar chain whose four bars are the first handle (L1), the crossover component (L2), the second handle (L3) and the crossbar (L4) pivotally connected respectively by:

a first joint (J1) between the first handle and the crossover component;

a second, crossover joint (J2) between the crossover component and the second handle;

a third joint (J3) between the second handle and the crossbar, and a fourth joint (J4) between the crossbar and the first handle, and wherein, upon application of a gripping force to the first and second handles, the first and second jaws separate from one another so as to separate the two components engaged therewith.

Preferably, the tool has mirror plane symmetry about an axis which extends transverse to an axis of the crossover joint. The symmetry eliminates shearing effects that may otherwise twist or deform the tool, potentially resulting in unsatisfactory contact with the components to be separated, or undesirable shearing forces. In an embodiment, the crossover component has a cleft therein in which said second handle is supported at said crossover joint.

In an embodiment, the position of the crossover joint with respect to the crossover component and/or the second handle is selectable so as to translate one of the jaws with respect to the other in order to accommodate differently sized components for separation. This enables the same tool to be used for many different lengths or positions of femoral stem, which is particularly useful in revision surgery when many different sizes and positions of implant may be encountered. In order to achieve this selectable position, the crossover component may include a plurality of apertures and said crossover joint comprises a removable hinge pin placed in a selected one of said apertures. Preferably said apertures are arranged in a line substantially perpendicular to a longitudinal axis of the tool. In another embodiment, the crossover joint comprises a lockable slip joint. In another embodiment, each of said crossover joint and said first joint comprises a lockable slip joint.

The first jaw may include a femoral stem grip capable of engaging a femoral stem through a lateral aperture when the tool approaches the stem radially and generally perpendicular to a longitudinal axis of the femoral stem. The femoral stem grip may have a generally tapered profile to enable it to engage with the shoulder or taper of many differently sized femoral stems.

The second jaw may include a femoral head grip capable of engaging the underside of a femoral head through a lateral aperture when the tool approaches the head radially and generally perpendicular to a longitudinal axis of a femoral stem to which the femoral head is attached. Preferably the femoral head grip has at least three points at which it can simultaneously engage the femoral head in order to provide a stable and balanced load to the femoral head during separation. The femoral head grip preferably has a generally circular profile. Both of the femoral head grip and the femoral stem grip may be chamfered. This helps the tool seat and centre itself on the components being separated, improving grip and stability.

It is preferred that the jaws remain relatively parallel during said separation. This can be achieved with the claimed tool as there is more of a translation element than a rotational element to the separation of the jaws and the separation takes place over a very short stroke.

In an embodiment, the tool further comprises biasing means, preferably a spring, arranged between said first and second handles in order to hold them in a default, relatively open, position before any gripping force is applied.

Safety features may be provided wherein one or more of said first handle, said second handle and said crossbar is provided with a safety endstop to avoid trapping fingers therebetween when a gripping force is applied. The endstop(s) can prevent the handles from being fully closed together.

The position of the third joint on the second handle is adjustable in order to adjust the mechanical advantage of the tool. This may be achieved using a screw mechanism which can be manually operated to cause the third joint to advance or retreat along the second handle. This adjustment allows a surgeon to position the tool's jaws accurately before applying a gripping force to the handles, to adjust the mechanism to a comfortable working configuration and to control the force applied. Compared to prior art mechanisms, the claimed tool is able to provide a very high mechanical advantage allowing the surgeon to exert extremely high separation forces on the components. Preferably the separating jaws are capable of applying a 7.5 kN force over a 0.3 mm stroke. The mechanical advantage of the tool may amplify the user's grip force by a factor of 20.

In an embodiment, one or more of the joints comprises a removable hinge pin. The third joint may comprise a pointed end of said crossbar engaging in a recess in said second handle.

Preferably, in use, the tool is positionable radially and generally perpendicular to a longitudinal axis of a femoral stem. This avoids the difficulty of space constraint near the top of the hip in the axial direction.

The surgical tool may further comprise a retaining cap for supporting and retaining a first component as it is separated from a second component. The retaining cap may be shaped to receive a femoral head.

In another aspect of the invention there is provided a method of separating first and second components having an interference fit therebetween using the tool of any of the preceding claims, the method comprising the steps of:
  a. approaching the first component in a radial direction, generally perpendicular to a longitudinal axis of the first component;
  b. engaging a shoulder or taper of the first component with said first jaw and engaging the underside of the second component with said second jaw;
  c. applying a gripping force to said handles in order to separate said jaws thus applying sufficient force to separate the second component from the first component.

The first component may be a femoral head and the second component may be a femoral stem. It is envisaged that other components having an interference fit therebetween may also be usefully separated using the tool described herein.

The method may further comprise the step of, before step a), selecting the position of the crossover joint with respect to the crossover component and/or the second handle.

The method may further comprise the step of, before or after step a), adjusting the position of the third joint on the second handle in order to set the mechanical advantage of the tool. This adjustment can both control the mechanical advantage and/or be used to fit the tool closely to the stem shoulder and femoral head at a comfortable hand position for the surgeon at step b).

BRIEF DESCRIPTION OF THE DRAWINGS

Embodiments of the invention are further described hereinafter, by way of example only, with reference to the accompanying drawings, in which.

DETAILED DESCRIPTION

Figure 1:
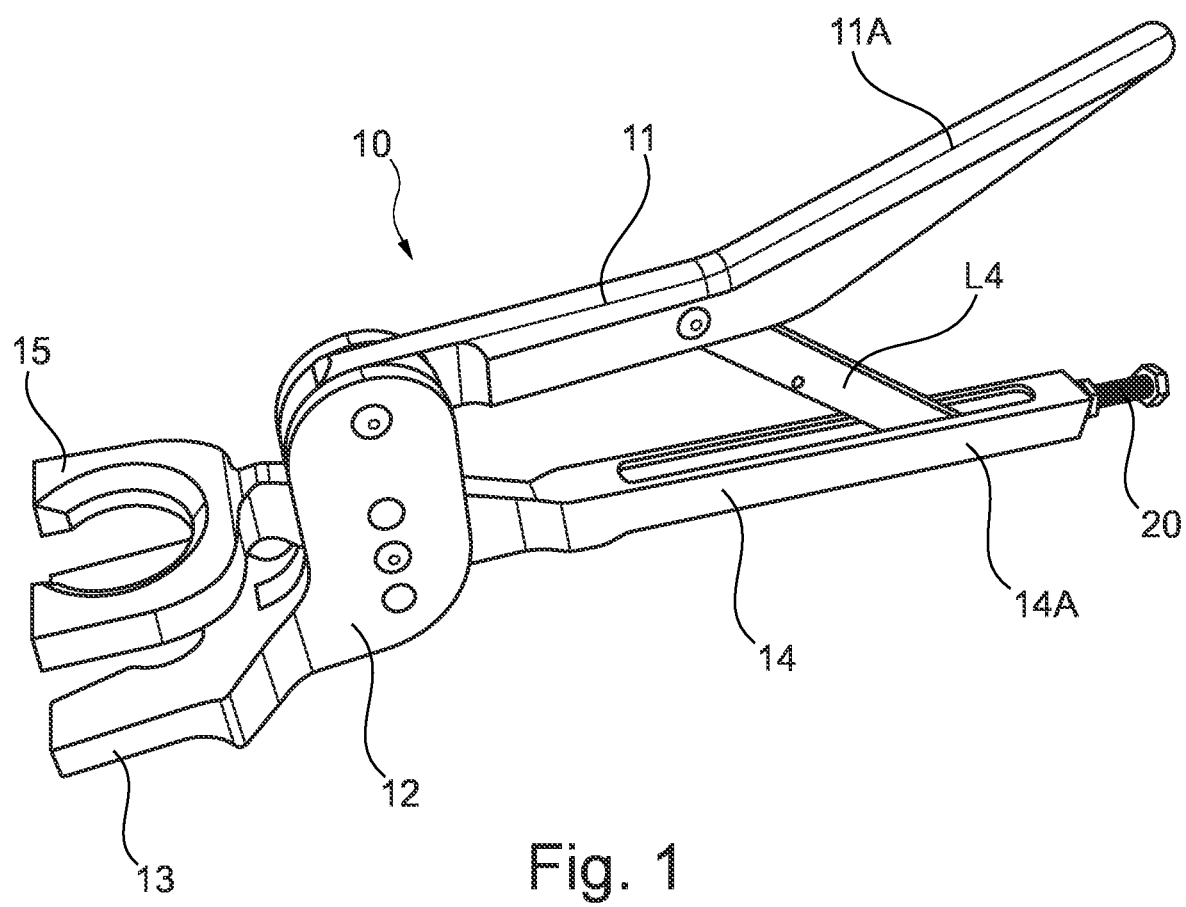
FIG. 1 is a perspective view of a surgical tool according to an embodiment of the invention.

FIGS. 1-4 show a surgical tool 10 according to one embodiment of the invention, the tool being suitable to separate a femoral head from a femoral stem.

In general terms, the surgical tool uses a four bar chain and crossover joint to provide a high mechanical advantage, converting a gripping force by the surgeon on two handles into a separating force at two jaws engaging the femoral head and stem.

A four bar chain arrangement is well known in many hand tools, for example in locking pliers, however it is normally used to provide a clamping or gripping action. In the claimed invention, the opposite is the case in that a separating action is provided.

The surgical tool 10 comprises a first handle 11, a second handle 14 and a crossbar L4 therebetween. The proximal ends of the handles, proximal of the crossbar L4, form gripping portions 11A, 14A respectively which are suitably sized that a surgeon may grip both gripping portions 11A, 14A simultaneously with one hand and apply a gripping force to bring the handles towards one another.

A crossover component 12 is provided which, in the illustrated embodiment, is generally right-angled. The crossover component 12 serves to join the first and second handles in a manner which will be explained in more detail below.

At the distal end of the surgical tool 10 is a first jaw 13 for engaging a femoral stem and a second jaw 15 for engaging a femoral head. The second jaw 15 may be integrally formed with the distal end of the second handle 14, or may be a separate component attached thereto. The first jaw 13 may be integrally formed with the distal end of the crossover component 12, or may be a separate component attached thereto.

Figure 2:
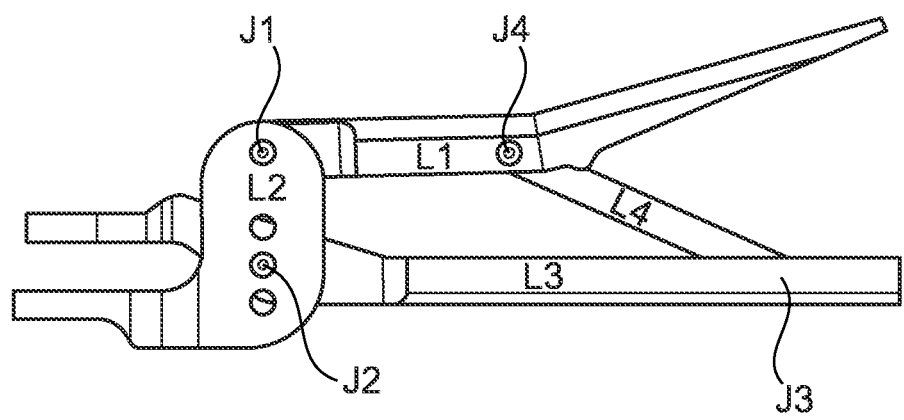
FIG. 2 is a side view of the surgical tool of FIG. 1.

As best shown in FIG. 2, the four bar chain is formed from four links or bars, namely:

L1 a distal portion of the first handle 11;
L2 a portion of the crossover component 12;
L3 a central portion of the second handle 14; and
L4 the crossbar.

The lengths of each of the links L1-L4 can be optimised according to the desired application of the tool, for example for separating a femoral head from a femoral stem.

The four bar chain includes four joints, namely:

J1 a first joint between the first handle 11 and the crossover component 12;
J2 a second, crossover, joint between the crossover component 12 and the second handle 14;
J3 a third joint between the second handle 14 and the crossbar L4; and
J4 a fourth joint between the crossbar L4 and the first handle 11.

Figure 3:
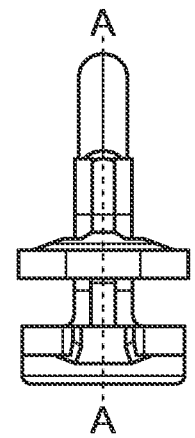
FIG. 3 is a front view of the surgical tool of FIG. 1.
Figure 4:
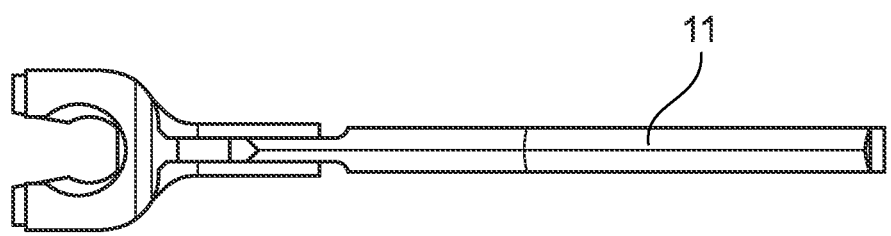
FIG. 4 is a top view of the surgical tool of FIG. 1.
Figure 5:
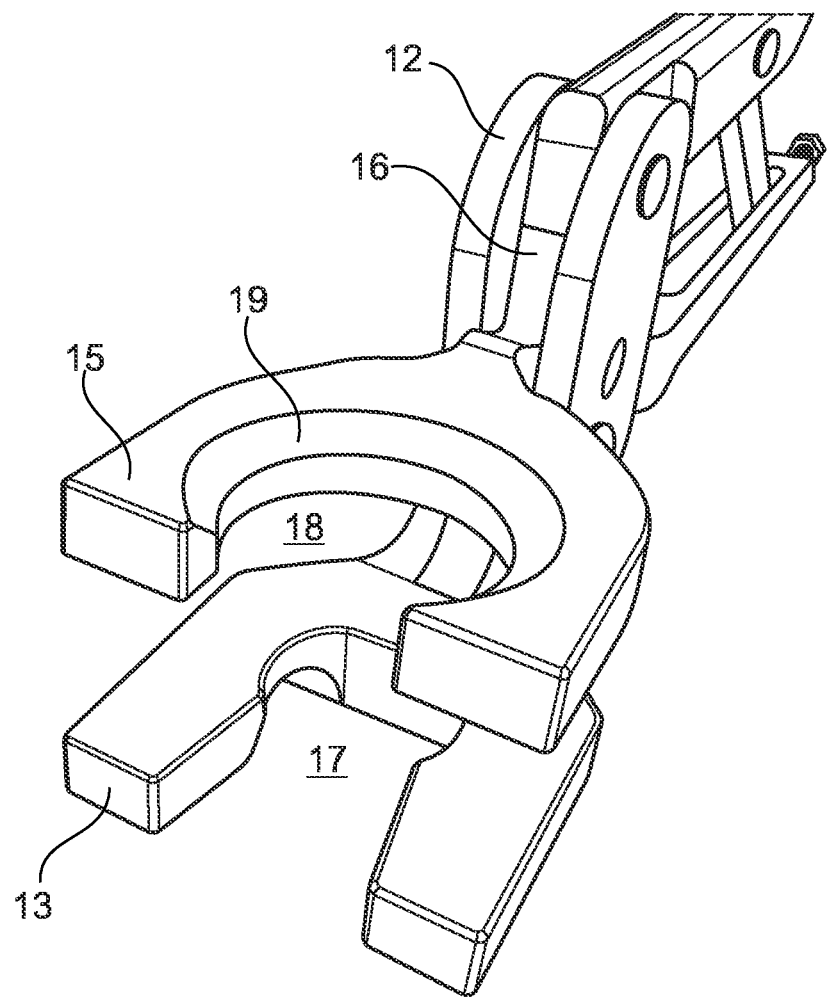
FIG. 5 shows the jaws of the surgical tool at a larger scale.

As can be seen from FIGS. 3 and 5, the tool 10 has mirror plane symmetry about a plane including line A-A in FIG. 3. The crossover joint J2 passes perpendicularly through this plane. The distal portion of the second handle 14 passes through a central cleft 16 in the crossover component 12 so this symmetry can be achieved.

Figure 8A:
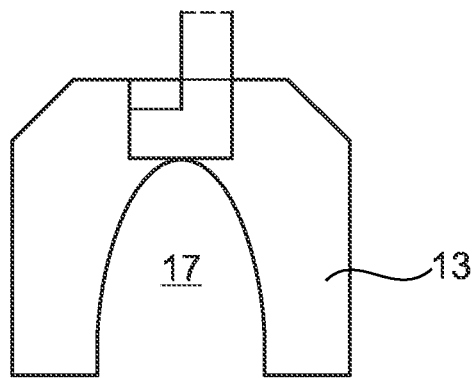
FIG. 8A is a top view of the jaw of FIG. 7.
Figure 8B:
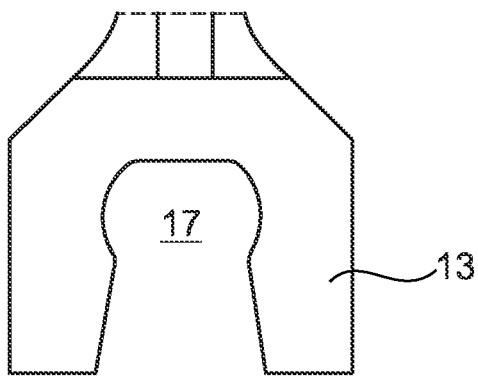
FIG. 8B is a top view of another embodiment of a jaw for engaging a femoral stem.

The jaws 13, 15 may also have mirror plane symmetry. The underside of the first jaw 13 includes a femoral stem grip which can engage a femoral stem in order to apply a separating force thereto. Femoral stems have a tapered trunnion (on which the femoral head is mounted) and a shoulder portion below the trunnion. The first jaw 13 is designed to engage the shoulder portion of the femoral stem. A stem grip recess 17 having a tapered profile can engage the shoulder of the femoral step at the contact region indicated in FIG. 9. The tapered profile enables many different sizes of femoral stem to be accommodated by the same tool. FIGS. 8A and 8B show example shapes for the stem grip recess 17.

In order to apply a separating force between the underside of the femoral head and the shoulder of the femoral stem, the tool 10 must be able to securely engage these points, particularly since the stem and head may be covered in fluid which will act as a lubricant.

The topside of the second jaw 15 includes a femoral head grip which can engage a femoral head in order to apply a separating force thereto. In order to apply a stable force to the femoral head, at least three points of contact are desired at which the jaw 15 can simultaneously engage the femoral head.

Figure 6:
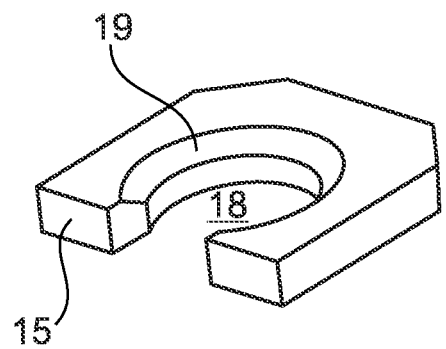
FIG. 6 shows an embodiment of a jaw for engaging a femoral head.
Figure 7:
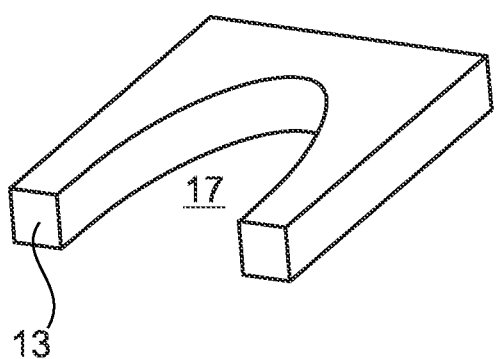
FIG. 7 shows an embodiment of a jaw for engaging a femoral stem.

Preferably, the femoral head grip is generally circular as shown best in FIGS. 5 and 6. A generally circular head grip recess 18 has a chamfered edge 19 which, not only helps centre and seat the tool on the femoral head but also allows different sizes of femoral head to be accommodated.

The femoral head grip and femoral stem grip each allow some freedom of rotation about all axes, without gripping either stem or head. As a result, the tool will not undesirably pull on the femoral stem in the event of a slight initial misalignment. A few degrees of rotation around the femur/stem axis are possible to deal with slight initial misalignment by the surgeon.

Figure 11C:
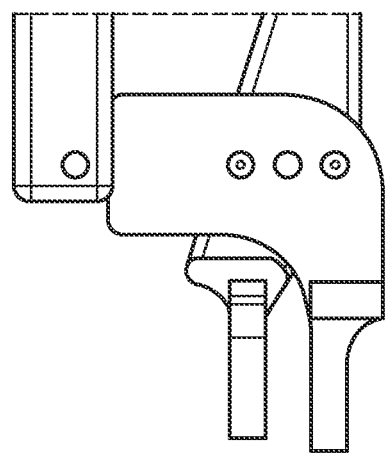
FIGS. 11A-11C are side views of part of the surgical tool, showing three embodiments for adjusting the position of the crossover joint with respect to the crossover component.
Figure 11B:
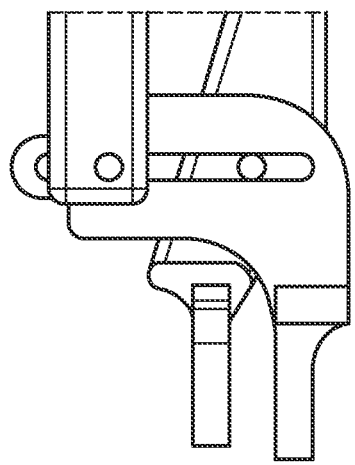
Figure 11A:
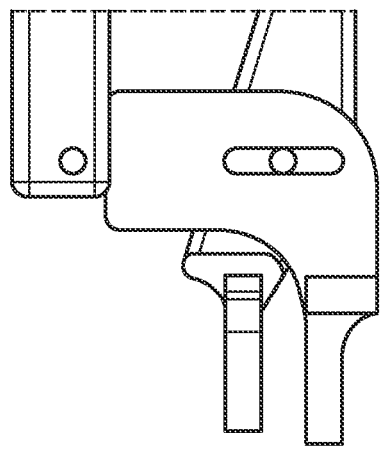

An advantage of the claimed invention is that the tool is adjustable. The starting position of the jaws 13, 15 with respect to one another can be adjusted in order to make an initial crude set up of the tool for a particular size of femoral head/stem. The starting position of the jaws 13, 15 is determined by the position of the crossover joint J2 with respect to the crossover component 12 and/or the second handle 14. As shown in FIGS. 11A-11C, the position of the crossover joint J2 can be changed in a number of ways which effect a translation of one jaw with respect to the other. Translation is preferable to rotation (e.g. simply opening the jaws wider) because of the advantages to stability of keeping the jaws relatively parallel to one another.

In FIG. 11A, a slip joint is used in which a slot in the crossover component 12 allows the crossover joint J2 to be positioned and locked anywhere within the slot. FIG. 11B shows an alternative in which a double slip joint is used, one for the crossover joint J2 and another for the first joint J1. A third embodiment is shown in FIG. 11C, this being the embodiment also shown in FIG. 1 et al, in which a plurality of apertures through the crossover component 12 are provided and the crossover joint J2 comprises a removeable hinge pin placed in a selected one of the apertures.

A further element of adjustability is provided by an adjustment screw 20 located at the proximal end of the second handle 14, as shown in FIG. 1. The distal end of the screw 20 abuts one end of the crossbar L4. Turning the screw 20 causes the crossbar L4 to advance or retreat along the second handle, which effectively moves the position of the third joint J3 of the four bar chain. In this way the mechanical advantage provided by the tool can be adjusted and the surgeon is able to adjust the starting position of the gripping portions 11A, 14A of the handles to a comfortable operating position.

The gripping portion 11A of the first handle 11 may be upwardly angled as shown in FIG. 1 so that, event when the handles are fully gripped together, it is not possible to accidentally trap fingers between them. In addition, a lug or safety endstop (not illustrated) may be provided in the vicinity of the crossbar L4 to limit the closure of the handles together.

Prototypes of the tool 10 have been manufactured from ABS (acrylonitrile butadiene styrene) and steel (316 stainless steel) respectively. Other metals or metal alloys or ceramics could be used. The jaws could be coated, for example with tungsten carbide, to improve their strength and longevity.

In another embodiment (not illustrated), a means of retaining and supporting the head as it is released is provided, potentially preventing it from being projected into the air when disengaged from the femoral stem. A curved arm may be attached to or included with the second jaw 15 which fit over the top of the femoral head, possibly adjustable with a screw or spring to fit it tightly to any size head. Femoral heads typically range in diameter from 22-44 mm.

A volute spring (not illustrated) could be employed between the first and second handles in order to bias the handles apart (and therefore to bias the jaws together) so that the default position for the jaws is close together so that the tool is ready for the next use.

Figure 9:
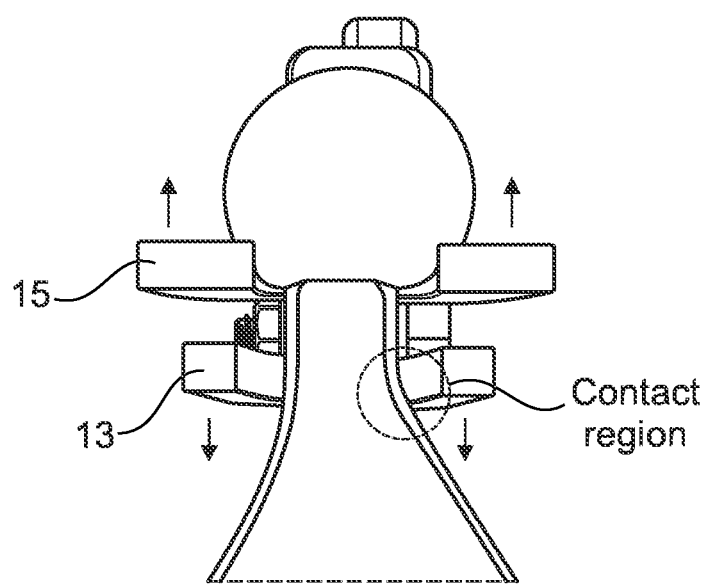
FIG. 9 is a front view of the surgical tool engaging a femoral head and femoral stem.
Figure 10:
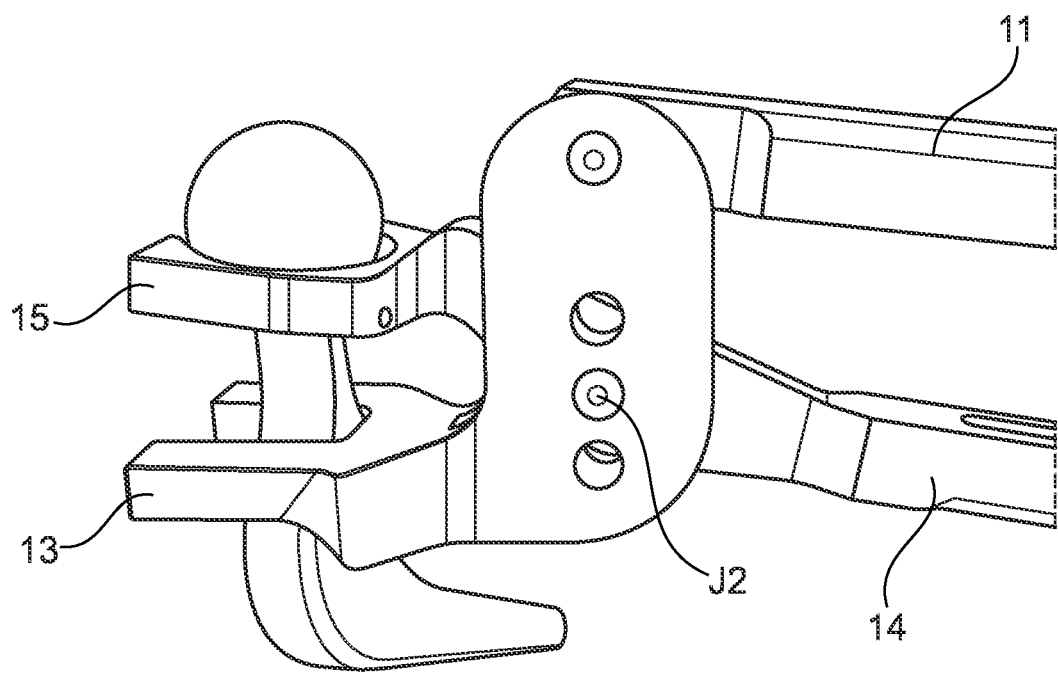
FIG. 10 is a side view of the surgical tool engaging and separating a femoral head and femoral stem.

Operation of the surgical tool 10 will now be described with reference to FIGS. 9 and 10 in particular.

When the surgeon needs to remove a femoral head from a femoral stem, the surgeon firstly checks the position of the crossover joint J2, moving if necessary, to ensure the jaws 13, 15 can adequately accommodate the particular size and shape of femoral head and stem involved. If the position of the crossover joint J2 needs to be moved, the hinge pin can be removed and replaced in another one of the line of apertures illustrated in FIG. 10.

The surgeon may also adjust the mechanical advantage of the tool using the adjustment screw 20 at the distal end of the second handle 14 in order to move the position of the third joint J3 to set a comfortable working position for the handles. The average surgeon's grip is most effective at a span of approximately 7 cm over a stroke of approximately 5 cm (from 8.5 cm to 3.5 cm span).

With the handles 11, 14 in their relatively open position, the jaws 13, 15 are relatively closed. In this starting position, the surgeon can approach the femoral head and stem from a radial or lateral direction, positioning the jaws 13, 15 between the underside of the femoral head and the shoulder of the femoral stem. Further adjustment of adjustment screw 20 may be used at this point to set the jaws into or close to initial contact with the femoral head and stem shoulder.

As the surgeon applies a gripping force to the handles 11, 14, the four bar chain causes the jaws 13, 15 to begin to move apart from one another. During this separation, the jaws 13, 15 remain relatively parallel to one another. As the jaw 15 makes contact with the underside of the femoral head, the chamfered edge 19 engages the femoral head, seating and centering the head and jaw 15 with respect to one another. The jaw 13 makes contact with the shoulder of the femoral stem, as shown in FIG. 9.

With both the femoral head and stem engaged by the tool 10, further application of a gripping force by the surgeon causes the application of a separating force by the tool between the underside of the femoral head and the shoulder of the femoral stem.

A short stroke, typically only 0.3 mm, is required to dislodge the femoral head from the tapered trunnion of the femoral stem. FIG. 9 shows the start of the separation process, the jaws 13, 15 moving the directions indicated by the arrows. FIG. 10 shows the end of the separation process, after which the femoral head can be simply lifted off the stem, having been dislodged by the surgical tool.

As the surgical tool 10 is reusable it is essential to properly sterilize and maintain the tool between uses. Immediately after surgery, the tool should be rinsed in warm water to remove any blood or bodily fluids. The tool may be submerged in a fresh neutral pH solvent and a soft brush used for more thorough cleaning. Then the tool may be placed in an ultrasound cleaner to completely remove contaminants, after which the tool may be air dried in a clean and dry environment. Before sterilization, the tool should be properly lubricated using a surgical lubricant such as instrument milk. The tool should then be placed in its open position in an autoclave for sterilization.

Testing of the surgical tool by orthopaedic consultants demonstrated, on an old hip replacement pair that was previously inseparable, that the head could be removed from the stem. The surgical tool 10 holds the stem in place as the head is removed. Another advantage over tools currently on the market is its compatibility with any size head, especially the over 40 mm head, which no known tool allows.

Although embodiments of the invention have been described in relation to removing a femoral head from a femoral stem, the surgical tool may be adapted for use in other surgical applications. For example the tool may be used to separate any two structures or components where a high force is required over a small stroke.

Throughout the description and claims of this specification, the term "mechanical advantage" refers to the amplification by the surgical tool of an input force provided by the user in order to output a greater force for separating the components.

Throughout the description and claims of this specification, the term "four bar chain" refers to a four bar chain, four bar mechanism or four bar linkage comprising four bars or links connected in a loop at four joints.

Throughout the description and claims of this specification, the terms "engaged" and "engagement" includes any connection, engagement, supporting, abutment or other positioning of components that enables transmission of mechanical force between the components.

Throughout the description and claims of this specification, the term "proximal" refers to the end of the surgical tool furthest from the jaws, i.e. the end nearest the surgeon.

Throughout the description and claims of this specification, the term "distal" refers to the end of the surgical tool nearest the jaws, i.e. the end furthest from the surgeon.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments.

The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

REFERENCE NUMERALS

10 Surgical tool
11 First handle
11A Gripping portion of first handle
L1 Portion of first handle in four bar chain
L1, L2, L3, L4 links or bars in four bar chain
J1, J2, J3, J4 joints in four bar chain
12 Crossover component
L2 Portion of crossover component in four bar chain
13 First jaw (for engaging stem)
14 Second handle
14A Gripping portion of second handle
L3 Portion of second handle in four bar chain
15 Second jaw (for engaging head)
L4 Crossbar
J1 First joint between first handle (L1) and crossover component (L2)
J2 Second, crossover joint between crossover component (L2) and second handle (L3)
J3 Third joint between second handle (L3) and cross bar (L4)
J4 Fourth joint (J4) between cross bar (L4) and first handle (L1)
16 cleft in the crossover component
17 stem grip recess
18 head grip recess
19 chamfered edge

The invention claimed is:

1. A surgical tool for separating two components, for example removing a femoral head from a femoral stem, the tool comprising:
   a. first and second handles with a crossbar therebetween, the handles being adapted to be moveable towards one another when gripped by a user;
   b. a crossover component;
   c. first and second jaws adapted to engage the two components to be separated wherein the first and second jaws are configured to apply a 7.5 kN force over a 0.3 mm stroke when engaged,
   wherein the first jaw is integral with or mounted on the crossover component and the second jaw is integral with or mounted on the second handle,
   wherein the tool comprises a four bar chain whose four bars are the first handle (L1), the crossover component (L2), the second handle (L3) and the crossbar (L4) pivotally connected respectively by:
   a first joint (J1) between the first handle and the crossover component;
   a second, crossover joint (J2) between the crossover component and the second handle;
   a third joint (J3) between the second handle and the crossbar, and
   a fourth joint (J4) between the crossbar and the first handle,
   and wherein, upon application of a gripping force to the first and second handles, the first and second jaws separate from one another so as to separate the two components engaged therewith.

2. The surgical tool of claim 1 wherein the tool has mirror plane symmetry about an axis which extends transverse to an axis of the crossover joint.

3. The surgical tool of claim 1 wherein the crossover component has a cleft therein in which said second handle is supported at said crossover joint.

4. The surgical tool of claim 1 wherein the position of the crossover joint with respect to the crossover component and/or the second handle is selectable so as to translate one of the jaws with respect to the other in order to accommodate differently sized components for separation.

5. The surgical tool of claim 4 wherein said crossover component includes a plurality of apertures and said crossover joint comprises a removable hinge pin placed in a selected one of said apertures.

6. The surgical tool of claim 4 wherein said crossover joint comprises a lockable slip joint.

7. The surgical tool of claim 1 wherein the second jaw includes a femoral head grip capable of engaging a femoral head through a lateral aperture when the tool approaches the head radially and generally perpendicular to a longitudinal axis of a femoral stem to which the femoral head is attached.

8. The surgical tool of claim 7 wherein the femoral head grip has at least three points at which it can simultaneously engage the femoral head.

9. The surgical tool of claim 1 wherein one or more of said first handle, said second handle and said crossbar is provided with a safety endstop to avoid trapping fingers therebetween when a gripping force is applied.

10. The surgical tool of claim 1 wherein the position of the third joint on the second handle is adjustable in order to adjust the mechanical advantage of the tool.

11. The surgical tool of claim 10 wherein the position of the third joint on the second handle is adjustable using a screw mechanism which can be manually operated to cause the third joint to advance or retreat along the second handle.

12. The surgical tool of claim 1 wherein the third joint comprises a pointed end of said crossbar engaging in a recess in said second handle.

13. The surgical tool of claim 1 wherein, in use, the tool is positionable radially and generally perpendicular to a longitudinal axis of a femoral stem.

14. The surgical tool of claim 1 further comprising a retaining cap for supporting and retaining a first component as it is separated from a second component.

15. The surgical tool of claim 14 wherein the retaining cap is shaped to receive a femoral head.

16. Method of separating first and second components having an interference fit therebetween using the tool of claim 1, the method comprising the steps of:
   a. approaching the first component in a radial direction, generally perpendicular to a longitudinal axis of the first component;
   b. engaging a shoulder or taper of the first component with said first jaw and engaging the underside of the second component with said second jaw;

applying a gripping force to said handles in order to separate said jaws thus applying sufficient force to separate the first component from the second component.

17. The method of claim 16 further comprising the step of, before step a), selecting the position of the crossover joint with respect to the crossover component and/or the second handle.

18. The method of claim 16 further comprising the step of, before or after step a), adjusting the position of the third joint on the second handle in order to set the mechanical advantage of the tool.

* * * * *